(12) United States Patent
Barasch et al.

(10) Patent No.: US 8,592,170 B2
(45) Date of Patent: Nov. 26, 2013

(54) HIGH MOLECULAR WEIGHT NGAL AS A BIOMARKER FOR CHRONIC KIDNEY DISEASE

(75) Inventors: Jonathan Barasch, New York, NY (US); Nicholas Barasch, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 251 days.

(21) Appl. No.: 12/922,047

(22) PCT Filed: Mar. 12, 2009

(86) PCT No.: PCT/US2009/036972
§ 371 (c)(1),
(2), (4) Date: Dec. 17, 2010

(87) PCT Pub. No.: WO2009/114699
PCT Pub. Date: Sep. 17, 2009

(65) Prior Publication Data
US 2011/0091912 A1    Apr. 21, 2011

Related U.S. Application Data

(60) Provisional application No. 61/035,841, filed on Mar. 12, 2008, provisional application No. 61/057,076, filed on May 29, 2008.

(51) Int. Cl.
G01N 33/573    (2006.01)
G01N 33/53    (2006.01)
G01N 33/564    (2006.01)
G01N 33/68    (2006.01)

(52) U.S. Cl.
USPC ............... 435/7.4; 435/7.1; 436/507; 436/86

(58) Field of Classification Search
None
See application file for complete search history.

(56) References Cited

U.S. PATENT DOCUMENTS

| | | | |
|---|---|---|---|
| 5,627,034 A | 5/1997 | Gould et al. | |
| 6,136,526 A | 10/2000 | Venge | |
| 6,447,989 B1 | 9/2002 | Comper | |
| 7,153,660 B2 | 12/2006 | Moses et al. | |
| 7,776,824 B2 | 8/2010 | Barasch et al. | |
| 2004/0219603 A1 | 11/2004 | Devarajan et al. | |
| 2005/0214219 A1 | 9/2005 | Green et al. | |
| 2005/0261191 A1 | 11/2005 | Barasch et al. | |
| 2005/0272101 A1 | 12/2005 | Devarajan et al. | |
| 2007/0037232 A1 | 2/2007 | Barasch et al. | |
| 2007/0105166 A1 | 5/2007 | Moses et al. | |
| 2007/0161125 A1 | 7/2007 | Rosenfeld et al. | |
| 2007/0196876 A1 | 8/2007 | Moses et al. | |
| 2007/0254370 A1 | 11/2007 | Barasch et al. | |
| 2008/0014604 A1 | 1/2008 | Devarajan et al. | |
| 2008/0014644 A1 | 1/2008 | Barasch et al. | |
| 2008/0050832 A1 | 2/2008 | Buechler et al. | |
| 2008/0057590 A1 | 3/2008 | Urdea et al. | |
| 2008/0090304 A1 | 4/2008 | Barasch et al. | |
| 2009/0123941 A1 | 5/2009 | Devarajan et al. | |
| 2009/0123970 A1 | 5/2009 | Tu et al. | |
| 2009/0142774 A1 | 6/2009 | Devarajan et al. | |
| 2009/0170143 A1 | 7/2009 | Uttenthal et al. | |
| 2009/0181407 A1 | 7/2009 | Devarajan et al. | |
| 2009/0215094 A1 | 8/2009 | Barasch et al. | |
| 2009/0269777 A1 | 10/2009 | Birkenmeyer et al. | |
| 2010/0015648 A1 | 1/2010 | Barasch et al. | |
| 2010/0028919 A1 | 2/2010 | Devarajan et al. | |
| 2010/0047837 A1 | 2/2010 | Devarajan et al. | |
| 2010/0122355 A1 | 5/2010 | Paragas et al. | |
| 2010/0184089 A1 | 7/2010 | Barasch et al. | |
| 2010/0227418 A1 | 9/2010 | Devarajan et al. | |
| 2010/0233728 A1 | 9/2010 | Devarajan et al. | |
| 2010/0234765 A1 | 9/2010 | Barasch et al. | |

FOREIGN PATENT DOCUMENTS

| | | |
|---|---|---|
| WO | WO-2004/088276 | 10/2004 |
| WO | WO-2005/107793 | 11/2005 |
| WO | WO-2005/121788 | 12/2005 |
| WO | WO-2006/066587 | 6/2006 |
| WO | WO-2007/044994 | 4/2007 |
| WO | WO-2007/047458 | 4/2007 |
| WO | WO-2009/114699 | 9/2009 |
| WO | WO-2010/045585 | 4/2010 |
| WO | WO-2010/148216 | 12/2010 |
| WO | WO-2012/068545 | 5/2012 |

OTHER PUBLICATIONS

Nickolas et al. "NGAL (Lcn2) monomer is associated with tubulointerstitial damage in chronic kidney disease", Kidney Int. Sep. 2012;82(6):718-22.*

Abergel, R.J., Clifton, M.C., Pizarro, J.C., Warner, J.A., Shuh, D.K., Strong, R.K., Raymond, K.N. (2008). The Siderocalin/Enterobactin Interaction: A Link between Mammalian Immunity and Bacterial Iron Transport. J. Am. Chem. Soc. 130, 11524-11534.

Ahlstrom A, Tallgren M, Peltonen S, Pettilä V. Evolution and predictive power of serum cystatin C in acute renal failure. Clin Nephrol. 2004:62:344-50.

Akerstrom B, Flower DR, Salier JP. (2000) Lipocalins: unity in diversity. Biochim Biophys Acta. 1482, 1-8.

Baliga R, Ueda N, Shah SV. (1993). Increase in bleomycin-detectable iron in ischaemia/reperfusion injury to rat kidneys. Biochem J. 291, 901-905.

Bander, SJ et al. "Long-term effects of 24-hour unilateral obstruction on renal function in the rat," Kidney Int 1985; 28:614.

Barasch, J & Mori, K: Cell biology: iron thievery. Nature, 432: 811-3, 2004.

(Continued)

Primary Examiner — Christine Foster
(74) Attorney, Agent, or Firm — Wilmer Cutler Pickering Hale and Dorr LLP

(57) ABSTRACT

A high molecular weight form of Ngal is provided which can be used to diagnose chronic kidney disease. High molecular weight Ngal is about 75 kDa to about 350 kDa, and comprises non-Ngal proteins, such as polymeric immunoglobulin receptor, alpha-2-macroglobulin and immunoglobulin heavy chain. Methods are disclosed for assessing high molecular weight Ngal in a diagnostic sample from a subject.

4 Claims, 4 Drawing Sheets

(56) References Cited

OTHER PUBLICATIONS

Bennett, M, Dent, CL, Ma, Q, Dastrala, S, Grenier, F, Workman, R, Syed, H, Ali, S, Barasch, J & Devarajan, P: Urine NGAL predicts severity of acute kidney injury after cardiac surgery: a prospective study. Clin J Am Soc Nephrol, 3: 665-73, 2008.

Berger T, Togawa A, Duncan GS, Elia AJ, You-Ten A, Wakeham A, et al. Lipocailn 2-deficient mice exhibit increased sensitivity to *Escherichia coli* infection but not to ischemia-reperfusion injury. Proc Nad Acad Sci USA. 2006; 103:1834-9.

Bogenschutz, O, Bohle, A, Batz, C, Wehrmann, M, Pressler, H, Kendziorra, H & Gartner, HV: IgA nephritis: on the importance of morphological and clinical parameters in the long term prognosis of 239 patients. Am J Nephrol, 10: 137-47, 1990.

Bohle, A, Mackensen Haen, S & von Gise, H: Significance of tubulointerstitial changes in the renal cortex for the excretory function and concentration ability of the kidney: a morphometric contribution. Am J Nephrol, 7: 421-33, 1987.

Bohle, A, Wehrmann, M, Bogenschutz, O, Batz, C, Muller, CA & Muller, GA: The pathogenesis of chronic renal failure in diabetic nephropathy. Investigation of 488 cases of diabetic glomerulosclerosis. Pathol Res Pract, 187: 251-9, 1991.

Bolignano D, Coppolino G, Campo S, Aloisi C, Nicocia G, Frisina N, Buemi M: Neutrophil gelatinase-associated lipocalin in patients with autosomal-dominant polycystic kidney disease. Am J Nephrol 27: 373-378, 2007.

Bolignano, D, Coppolino, G, Campo, S, Aloisi, C, Nicocia, G, Frisina, N & Buemi, M: Urinary neutrophil gelatinase associated lipocalin (NGAL) is associated with severity of renal disease in proteinuric patients. Nephrol Dial Transplant, 23: 414-6, 2008.

Bolignano, D, Lacquaniti, A, Coppolino, G, Campo, S, Arena, A & Buemi, M: Neutrophil Gelatinase Associated Lipocalin Reflects the Severity of Renal Impairment in Subjects Affected by Chronic Kidney Disease. Kidney Blood Press Res, 31: 255-258, 2008.

Brenner, BM, Cooper, ME, de Zeeuw, D, Keane, WF, Mitch, WE, Parving, HH, Remuzzi, G, Snapinn, SM, Zhang, Z & Shahinfar, S: Effects of losartan on renal and cardiovascular outcomes in patients with type 2 diabetes and nephropathy. N Engl J Med, 345: 861-9, 2001.

Bundgaard JR, Sengelov H, Borregaard N, Kjeldsen L. Molecular cloning and expression of a cDNA encoding NGAL: a lipocalin expressed in human neutrophils. Biochem Biophys Res Commun. 1994;202:1468-75.

Cooper MA, Buddington B, Miller NL, Alfrey AC. (1995) Urinary iron speciation in nephrotic syndrome. Am J Kidney Dis. 25, 314-9.

D'Amico, G, Ferrario, F & Rastaldi, MP: Tubulointerstitial damage in glomerular diseases: its role in the progression of renal damage. Am J Kidney Dis, 26: 124-32, 1995.

de Vries B, Walter SJ, Wolfs TG, Hochepied T, Räbinä J, Heeringa P, et al. Exogenous alpha-1-acid glycoprotein protects against renal ischemia-reper- fusion injury by inhibition of inflammation and apoptosis. Transplantation. 2004:78:1116-24.

de Zeeuw, D, Ramjit, D, Zhang, Z, Ribeiro, AB, Kurokawa, K, Lash, JP, Chan, J, Remuzzi, G, Brenner, BM & Shahinfar, S: Renal risk and renoprotection among ethnic groups with type 2 diabetic nephropathy: a post hoc analysis of RENAAL. Kidney Int, 69: 1675-82, 2006.

Devireddy, L.R., Gazin, C., Zhu, X., Green, M.R. (2005). A Cell-Surface Receptor for Lipocalin 24p3 Selectively Mediates Apoptosis and Iron Uptake. *Cell*. 123, 1293-1305.

Ding, et al., "Urinary neutrophil gelatinase associated lipocalin (NGAL) is an early biomarker for renal tubulointerstitial injury in IgA nephropathy," Clin Immunol, 123: 227-34, 2007.

Doneanu et al., "Charactirization of a noncovalent lipocalin complex by liquid chromatography/electrospray inoization mass spectrometry," J. Biomol Tech, vol. 15(3), pp. 208-212 (Sep. 2004).

Eddy, AA, McCulloch, L, Liu, E & Adams, J: A relationship between proteinuria and acute tubulointerstitial disease in rats with experimental nephrotic syndrome. Am J Pathol, 138: 1111-23, 1991.

Eddy, AA: Progression in chronic kidney disease. Adv Chronic Kidney Dis, 12: 353-65, 2005.

Eddy, AA: Proteinuria and interstitial injury. Nephrol Dial Transplant, 19: 277-81, 2004.

Flo, TH, Smith, KD, Sato, S, Rodriguez, DJ, Holmes, MA, Strong, RK, Akira, S & Aderem, A: Lipocalin 2 mediates an innate immune response to bacterial infection by sequestrating iron. Nature, 432: 917-21, 2004.

Fluckinger, et al. (2004). Human tear lipocalin exhibits antimicrobial activity by scavenging microbial siderophores. Antimicrob Agents Chemother. 48, 3367-3372.

Gaspari, F, Perico, N, Ruggenenti, P, Mosconi, L, Amuchastegui, CS, Guerini, E, Daina, E & Remuzzi, G: Plasma clearance of nonradioactive iohexol as a measure of glomerular filtration rate. J Am Soc Nephrol, 6: 257-63, 1995.

Goetz, D.H., Holmes, M.A., Borregaard, N., Bluhm, M.E., Raymond, K.N., Strong, R.K. (2002). The Neutrophil Lipocalin NGAL is a Bacteriostatic Agent that Interferes with Siderophore-Mediated Iron Acquisition. Mol. Cell 10, 1033-1043.

Goetz, D.H., Willie, S.T., Armen, R.S., Bratt, T., Borregaard, N., Strong, R.K. (2000). Ligand preference inferred from the structure of neutrophil gelatinase associated lipocalin. Biochemistry 39, 1935-1941.

Gonzalez-Michaca L, Farrugia G, Croatt AJ, Alam J, Nath KA. (2004) Heme: a determinant of life and death in renal tubular epithelial cells. Am J Physiol Renal Physiol. 286, F370-7.

Gwira JA, Wei F, Ishibe S, Ueland JM, Barasch J, Cantley LG: Expression of neutrophil gelatinase-associated lipocalin regulates epithelial morphogenesis in vitro. J Biol Chem 280: 7875-7882, 2005.

Han WK, Bailly V, Abichandani R, Thadhani R, Bonventre JV. Kidney Injury Molecule-1 (KIM-1): a novel biomarker for human renal proximal tubule injury. Kidney Int. 2002:62:237-44.

Han WK, Waikar SS, Johnson A, Betensky RA, Dent CL, Devarajan P, et al. Urinary biomarkers in the early diagnosis of acute kidney injury. Kidney Int. 2008:73:863-9.

Harris DC, Tay C, Nankivell BJ. (1994) Lysosomal iron accumulation and tubular damage in rat puromycin nephrosis and ageing. Clin Exp Pharmacol Physiol. 21, 73-81.

He, JC, Husain, M, Sunamoto, M, D'Agati, VD, Klotman, ME, Iyengar, R & Klotman, PE: Nef stimulates proliferation of glomerular podocytes through activation of Src-dependent Stat3 and MAPK1,2 pathways. *J Clin Invest*, 114: 643-51, 2004.

Herget-Rosenthal S, Marggraf G, Hüsing J, Göring F, Pietruck F, Janssen O, et al. Early detection of acute renal failure by serum cystatin C. Kidney Int. 2004:66:1115-22.

Herget-Rosenthal S, Poppen D, Hüsing J, Marggraf G, Pietruck F, Jakob HG, et al. Prognostic value of tubular proteinuria and enzymuria in nonoliguric acute tubular necrosis. Clin Chem. 2004:50:552-8.

Hill, GS, Delahousse, M, Nochy, D, Tomkiewicz, E, Remy, P, Mignon, F & Mery, JP: A new morphologic index for the evaluation of renal biopsies in lupus nephritis. Kidney Int, 58: 1160-73, 2000.

Hoette, T. M., Abergel, R. J., Xu, J.; Strong, R. K., Raymond, K. N. (2008). "The role of electrostatics in siderophore recognition by the immunoprotein Siderocalin". J. Am. Chem. Soc. 130, 17584-17592.

Holmes, M.A., Paulsene, W., Jide, X., Ratledge, C., Strong, R.K. (2005). Siderocalin (Lcn 2) also binds carboxymycobactins, potentially defending against mycobacterial infections through iron sequestration. Structure 13, 29-41.

Howard, R.L., Buddington, B., Alfrey, A.C. (1991). Urinary albumin, transferrin and iron excretion in diabetic patients. Kidney Int. 40, 923-926.

Hunsicker, LG, Adler, S, Caggiula, A, England, BK, Greene, T, Kusek, JW, Rogers, NL & Teschan, PE: Predictors of the progression of renal disease in the Modification of Diet in Renal Disease Study. Kidney Int, 51: 1908-19, 1997.

Hvidberg V, Jacobsen C, Strong RK, Cowland JB, Moestrup SK, Borregaard N. (2005). The endocytic receptor megalin binds the iron transporting neutrophil-gelatinase-associated lipocalin with high affinity and mediates its cellular uptake. FEBS Lett. 579, 773-7.

Iannetti A, Pacifico F, Acquaviva R, Lavorgna A, Crescenzi E, Vascotto C, Tell G, Salzano AM, Scaloni A, Vuttariello E, Chiappetta G, Formisano S, Leonardi A: The neutrophil gelatinase-associated

(56) References Cited

OTHER PUBLICATIONS lipocalin (NGAL), a NF-B-regulated gene, is a survival factor for thyroid neoplastic cells. Proc Natl Acad Sci USA 105: 14058-14063, 2008.

Jones, R.L., Peterson, C.M., Grady, R.W., Cerami, A. (1980). Low molecular weight iron-binding factor from mammalian tissue that potentiates bacterial growth. J. Exp. Med. 151, 418-428.

Kim, S., Vermeulen, R., Waidyanatha, S., Johnson, B.A., Lan, Q., Rothman, N., Smith, M.T., Zhang, L., Li, G., Shen, M., Yin, S., Rappaport, S.M. (2006). Using urinary biomarkers to elucidate dose-related patterns of human benzene metabolism.Carcinogenesis 27, 772-781.

Lars Kjeldsen et al., "Characterization of two ELISAs for NGAL, a newly described lipocalin in human neutrophils", Journal of Immunological Methods, vol. 198, 155-16, (1996).

Levey, AS, Bosch, JP, Lewis, JB, Greene, T, Rogers, N & Roth, D: A more accurate method to estimate glomerular filtration rate from serum creatinine: a new prediction equation. Modification of Diet in Renal Disease Study Group. Ann Intern Med, 130: 461-70, 1999.

Lewis, EJ, Hunsicker, LG, Clarke, WR, Berl, T, Pohl, MA, Lewis, JB, Ritz, E, Atkins, RC, Rohde, R & Raz, I: Renoprotective effect of the angiotensin receptor antagonist irbesartan in patients with nephropathy due to type 2 diabetes. N Engl J Med, 345: 851-60, 2001.

Li, J.Y., Paragas, N., Ned, R.M., Qiu, A., Viltard, M., Leete, T., Drexler, I.R., Chen, X., Sanna-Cherchi, S., Mohammed, F., Williams, D., Lin, C. S., Schmidt-Ott, K.M., Andrews, N. C. (2009). Scara5 Is a Ferritin Receptor Mediating Non-Transferrin Iron Delivery. Dev. Cell 16, 35-46.

Liangos O, Perianayagam MC, Vaidya VS, Han WK, Wald R, Tighiouart H, et al. Urinary N-acetyl-beta-(D)-glucosaminidase activity and kidney injury molecule-1 level are associated with adverse outcomes in acute renal failure. J Am Soc Nephrol. 2007:18:904-12.

Mackensen Haen, S, Bohle, A, Christensen, J, Wehrmann, M, Kendziorra, H & Kokot, F: The consequences for renal function of widening of the interstitium and changes in the tubular epithelium of the renal cortex and outer medulla in various renal diseases. Clin Nephrol, 37: 70-7, 1992.

Magil, AB: Tubulointerstitial lesions in human membranous glomerulonephritis: relationship to proteinuria. Am J Kidney Dis, 25: 375-9, 1995.

Metcalfe, W: How does early chronic kidney disease progress? A background paper prepared for the UK Consensus Conference on early chronic kidney disease. Nephrol Dial Transplant, 22 Suppl 9: ix26-30, 2007.

Mishra J, Dent C, Tarabishi R, Mitsnefes MM, Ma Q, Kelly C, Ruff SM, Zahedi K, Shao M, Bean J, Mori K, Barasch J, Devarajan P. (2005). Neutrophil gelatinase-associated lipocalin (NGAL) as a biomarker for acute renal injury after cardiac surgery. Lancet. 365, 1231-8.

Mishra J, Ma Q, Prada A, Mitsnefes M, Zahedi K, Yang J, Barasch J, Devarajan P: Identification of neutrophil gelatinase-associated lipocalin as a novel early urinary biomarker for ischemic renal injury. J Am Soc Nephrol 14: 2534-2543, 2003.

Mishra, J, Ma, Q, Kelly, C, Mitsnefes, M, Mori, K, Barasch, J & Devarajan, P: Kidney NGAL is a novel early marker of acute injury following transplantation. Pediatr Nephrol, 21: 856-63, 2006.

Mishra, J, Mori, K, Ma, Q, Kelly, C, Barasch, J & Devarajan, P: Neutrophil gelatinase associated lipocalin: a novel early urinary biomarker for cisplatin nephrotoxicity. Am J Nephrol, 24: 307-15, 2004.

Mishra, J, Mori, K, Ma, Q, Kelly, C, Yang, J, Mitsnefes, M, Barasch, J & Devarajan, P: Amelioration of ischemic acute renal injury by neutrophil gelatinase-associated lipocalin. *J Am Soc Nephrol*, 15: 3073-82, 2004.

Mitsnefes MM et al. (2006) Serum neutrophil gelatinase-associated lipocalin as a marker of renal function in children with chronic kidney disease. *Pediatr Nephrol*. 22:101-8).

Mori K and Nakao K. (2007) Neutrophil gelatinase-associated lipocalin as the real-time indicator of active kidney damage. Kidney International 71:967-970.

Mori, K, Lee, HT, Rapoport, D, Drexler, IR, Foster, K, Yang, J, Schmidt-Ott, KM, Chen, X, Li, JY, Weiss, S, Mishra, J, Cheema, FH, Markowitz, G, Suganami, T, Sawai, K, Mukoyama, M, Kunis, C, D'Agati, V, Devarajan, P & Barasch, J: Endocytic delivery of lipocalin-siderophore-iron complex rescues the kidney from ischemia-reperfusion injury. J Clin Invest, 115: 610-21, 2005.

Nankivell BJ, Boadle RA, Harris DC: Iron accumulation in human chronic renal disease. Am J Kidney Dis 20: 580-584, 1992.

National Kidney Foundation. K/DOQI clinical practice guidelines for chronic kidney disease: evaluation, classification, and stratification. Am J Kidney Dis. 2002;39:Sl-266.

Nelson A.L., Barasch, J.M., Bunte, R.M., Weiser, J.N. (2005). Bacterial colonization of nasal mucosa induces expression of siderocalin, an iron-sequestering component of innate immunity. Cell Microbiol. 7, 1404-1417.

Nguyen MT, Harris N, Kathman T, Dent C, Devarajan P. Novel early biomarkers of acute kidney injury [Abstract]. J Am Soc Nephrol. 2006;17:49A.

Nickolas, T.L., O'Rourke, M.J., Yang, J., Sise, M.E., Canetta, P.A., Barasch, N., Buchen, C., Khan, F., Mori, K., Giglio, J., Devarajan, P., Barasch, J. (2008). Sensitivity and specificity of a single emergency department measurement of urinary neutrophil gelatinase-associated lipocalin for diagnosing acute kidney injury. Annals Internal Medicine. 148, 810-819.

Paller, M.S., Hedlund, B.E. (1988). Role of iron in postischemic renal injury in the rat. Kidney Int. 34, 474-480.

Parikh CR, Abraham E, Ancukiewicz M, Edelstein CL. Urine IL-18 is an early diagnostic marker for acute kidney injury and predicts mortality in the intensive care unit. J Am Soc Nephrol. 2005; 16:3046-52.

Parikh CR, Jani A, Melnikov VY, Faubel S, Edelstein CL. Urinary interleukin-18 is a marker of human acute tubular necrosis. Am J Kidney Dis. 2004; 43:405-14.

Parikh CR, Jani A, Mishra J, Ma Q, Kelly C, Barasch J, et al. Urine NGAL and IL-18 are predictive biomarkers for delayed graft function following kidney transplantation. Am J Transplant. 2006:6:1639-45.

Parikh CR, Mishra J, Thiessen-Philbrook H, Dursun B, Ma Q, Kelly C, et al. Urinary IL-18 is an early predictive biomarker of acute kidney injury after cardiac surgery. Kidney Int. 2006:70:199-203.

Perrone, RD, Madias, NE & Levey, AS: Serum creatinine as an index of renal function: new insights into old concepts. Clin Chem, 38: 1933-53, 1992.

Playford RJ, Belo A, Poulsom R, Fitzgerald AJ, Harris K, Pawluczyk I, Ryon J, Darby T, Nilsen-Hamilton M, Ghosh S, Marchbank T: Effects of mouse and human lipocalin homologues 24p3/lcn2 and neutrophil gelatinase-associated lipocalin on gastrointestinal mucosal integrity and repair. Gastroenterology 131: 809-817, 2006.

Prinsen, B.H., de Sain-van der Velden, M.G., Kaysen, G.A., Strayer, H.W., van Rijn, H.J., Stellaard, F., Berger, R., Rabelink, T.J. (2001). Transferrin synthesis is increased in nephrotic patients insufficiently to replace urinary losses. J. Am. Soc. Nephrol. 12, 1017-25.

Qu Q, Melikian AA, Li G, Shore R, Chen L, Cohen B, Yin S, Kagan MR, Li H, Meng M, Jin X, Winnik W, Li Y, Mu R, Li K. (2000). Validation of biomarkers in humans exposed to benzene: urine metabolites Am J Ind Med. 37, 522-31.

Remuzzi, G, Ruggenenti, P & Benigni, A: Understanding the nature of renal disease progression. Kidney Int, 51: 2-15, 1997.

Richardson, D.R. (2005). 24p3 and Its Receptor: Dawn of a New Iron Age? Cell 123, 1175-1177.

Risdon, RA, Sloper, JC & De Wardener, HE: Relationship between renal function and histological changes found in renal biopsy specimens from patients with persistent glomerular nephritis. Lancet, 2: 363-6, 1968.

Saweirs, WW & Goddard, J: What are the best treatments for early chronic kidney disease? A background paper prepared for the UK Consensus Conference on early chronic kidney disease. Nephrol Dial Transplant, 22 Suppl 9: ix31-38, 2007.

Schmidt-Ott KM et al. (2007) Dual action of neutrophil gelatinase-associated lipocalin. J Am Soc Nephrol. 18:407-13.

(56) References Cited

OTHER PUBLICATIONS

Schmitt, H, Cavalcanti de Oliveira, V & Bohle, A: Tubulo interstitial alterations in type I membranoproliferative glomerulonephritis. An investigation of 259 cases. Pathol Res Pract, 182: 6-10, 1987.
Soler-Garcia AA, Johnson D, Hathout Y, Ray PE. (2009). Iron-related proteins: candidate urine biomarkers in childhood HIV-associated renal diseases. Clin J Am Soc Nephrol. 4, 763-71.
Stone DH, Al-Badawi H, Conrad MF, Stoner MC, Entabi F, Cambria RP, et al. PJ34, a poly-ADP-ribose polymerase inhibitor, modulates renal injury after thoracic aortic ischemia/reperfusion. Surgery. 2005; 138:368-74.
Vaidya VS, Ferguson MA, Bonventre JV:Biomarkers of acute kidney injury. Annu Rev Pharmacol Toxicol 48: 463-493, 2008.
Vera T, Henegar JR, Drummond HA, Rimoldi JM, Stec DE. Protective effect of carbon monoxide-releasing compounds in ischemia-induced acute renal failure. J Am Soc Nephrol. 2005:16:950-8.
Vleming, LJ, de Fijter, JW, Westendorp, RG, Daha, MR, Bruijn, JA & van Es, LA: Histomorphometric correlates of renal failure in IgA nephropathy. Clin Nephrol, 49: 337-44, 1998.
Wagener, G, Jan, M, Kim, M, Mori, K, Barasch, JM, Sladen, RN & Lee, HT: Association between increases in urinary neutrophil gelatinase-associated lipocalin and acute renal dysfunction after adult cardiac surgery. *Anesthesiology*, 105: 485-91, 2006.
Wang H, Nishiya K, Ito H, Hosokawa T, Hashimoto K, Moriki T. (2001) Iron deposition in renal biopsy specimens from patients with kidney diseases. Am J Kidney Dis. 38, 108-44.
Wehrmann, M, Bohle, A, Held, H, Schumm, G, Kendziorra, H & Pressler, H: Long-term prognosis of focal sclerosing glomerulonephritis. An analysis of 250 cases with particular regard to tubulointerstitial changes. *Clin Nephrol*, 33: 115-22, 1990.
Wei F, Karihaloo A, Yu Z, Marlier A, Seth P, Shibazaki S, Wang T, Sukhatme VP, Somlo S, Cantley LG: Neutrophil gelatinase-associated lipocalin suppresses cyst growth by Pkd1 null cells in vitro and in vivo. Kidney Int 74: 1310-1318, 2008.
Wu ZL, Paller MS. (1994) Iron loading enhances susceptibility to renal ischemia in rats. Ren Fail. 16, 471-80.
Yang, J., Goetz, D., Li, J.Y., Wang, W., Mori, K., Setlik, D., Du, T., Erdjument-Bromage, H., Tempst, P., Strong, R., Barasch, J. (2002). An iron delivery pathway mediated by a lipocalin. Mol Cell 10, 1045-1056.
Zager, R.A. (1992). Combined mannitol and deferoxamine therapy for myohemoglobinuric renal injury and oxidant tubular stress. Mechanistic and therapeutic implications. J. Clin. Invest. 90, 711-719.
Zappitelli M, Washburn KK, Arikan AA, Loftis L, Ma Q, Devarajan P, et al. Urine neutrophil gelatinase-associated lipocalin is an early marker of acute kidney injury in critically ill children: a prospective cohort study. Crit Care. 2007;II:R84.
Barr et al., Urinary creatinine concentrations in the U.S. population: implications for urinary biologic monitoring measurements. Environmental Health Perspectives 113: 192-200 (2005).
BioPorto Diagnostics A/S, "Human NGAL Rapid ELISA Kit (Kit 037)", Revision:, Sep. 2010, Retrieve from internet <url: http://www.bioporto.com/products/bioporto_diagnostics/ngal_elisa_kits/ngal_rapid_elisa_kit_ce_ivd>, 4 pages.
BioPorto Diagnostics A/S, "NGAL Rapid ELISA Kit (Kit 037)", Revision: NR2007-12-EN, Dec. 2007, Retrieve from internet <url:https://www.piercenet.com/files/kit037.PDF>, 84 pages.
DeLong ER, et al., Comparing the areas under two or more correlated receiver operating characteristic curves: a nonparametric approach. Biometrics, 44:837-45 (1988).
Hall et al., IL-18 and urinary NGAL predicts dialysis and graft recovery after kidney transplantation, J. Am. Soc. Nephrol. vol. 21, No. 1, pp. 189-197 (2010)—ePub 27 Sep. 2009.
Han et al., "Kidney Injury Molecule-1: A novel biomarker for human renal proximal tubule injury," Kidney international, vol. 62, pp. 237-244 (2002).
Ichimura et al., "Kidney Injury Molecule-1(KIM-1), a Putative Epithelial Cell adhesion Molecule Containing a Novel immunoglobulin domain, is Up-regulated in Renal Cells after Injury," the Journal of biological Chemistry, vol. 273, pp. 4135-4142 (1998).
Kribben, A., et al., "Pathophysiology of acute renal failure", J. Nephrol, 12 Supplement, 2, S142-S151 (1999).
Makris et al., "Urinary neutrophil gelatinase-associated lipocalin (NGAL) as an early marker of acute kidney injury in critically ill multiple trauma patients", Clin Chem Lab Med, vol. 47, pp. 79-82 (2009).
Monier et al., Gelatinase isoforms in urine from bladder cancer patients, Clinica Chimica Acta 299:11-23 (2000).
Paragas et al., Urinary NGAL marks cystic disease in HIV-associated nephropathy, J Am Soc Nephrol., 20(8):1687-92 (2009).
Sise et al., "Urine neutrophil gelatinase-associated lipocalin identifies unilateral and bilateral urinary tract obstruction," Nephrol Dial Transplant, vol. 26, pp. 4132-4135 (2011).
Yan et al., The High Molecular Weight Urinary Matrix Metalloproteinase (MMP) Activity Is a Complex of Gelatinase B/MMP-9 and Neutrophil Gelatinase-associated Lipocalin (NGAL),J. Biol. Chem., 276(40): 37258-37265 (2001).
International Search Report mailed on Mar. 29, 2012 for International Patent Application No. PCT/US2011/061531, 2 pages.
International Search Report and Written Opinion mailed on Feb. 24, 2010 for International Patent Application No. PCT/US09/36972 filed Mar. 12, 2009.
Xu, S. Y., et al., "Serum measurements of human neutrophil lipocalin (HNL) discriminate between acute bacterial and viral infections", Scand. J. Clin. Lab Invest, 1995, vol. 55, pp. 125-131.
Lerma, Edger, et al., "Current Diagnosis & Treatment Nephrology & Hypertension", McGraw Hill Education, Chapter 36, pp. 313-319, Table of Contents, 2 pages, (Feb. 2009).
Devarajan, Prasad, "Neutrophil gelatinase-associated lipocalin: new paths for an old shuttle", Cancer Therapy, 2007, Issue 5(B), pp. 463-470.
Borregaard, Niels, et al., "Neutrophil gelatinase-associated lipocalin, a siderophore-binding eukaryotic protein", BioMetals, 2006, vol. 19, pp. 211-215.
Wagener G et al. (2008) Increased incidence of acute kidney injury with aprotinin use during cardiac surgery detected with urinary NGAL. Am J Nephrol. 28:576-582.
Dent et al., "Plasma neutrophil gelatinase-assocaited lipocalin predicts acute kidney injury, morbidity and mortality after pediatric cardiac surgery: a prospective unconttrolled cohort study," Critical Care, vol. 11, R127, 8 pages (2007).
Kjeldsen et al., "Isolation and primary structure of NGAL, a novel protein associated with human neutrophil gelatinase," The journal of Biological chemistry, vol. 268, pp. 10425-10432 (May 15, 1993).
Rubinstein et al., "The novel role of neutrophil gelatinase-B associated lipocalin (NGAl)/Lipocalin-2 as a biomarker for lupus nephritis," Autoimmunity reviews, vol. 7, pp. 229-234 (Jan. 2008).
Supplementary European Search report mailed on Oct. 4, 2011 for European Application No. EP 09720017.4 filed on Mar. 12, 2009, 7 pages.
Simel DL, Samsa GP, Matchar DB. Likelihood ratios with confidence: sample size estimation for diagnostic test studies. J Clin Epidemiol., vol. 44:763-70. (1991).

\* cited by examiner

HIGH MOLECULAR WEIGHT NGAL AS A BIOMARKER FOR CHRONIC KIDNEY DISEASE

This application is a U.S. National Phase Application under 35 U.S.C. 371 of International Patent Application No. PCT/US09/36972 filed Mar. 12, 2009, which claims priority to U.S. Provisional Application No. 61/035,841 filed on Mar. 12, 2008, and U.S. Provisional Application No. 61/057,076 filed on May 29, 2008, both of which are hereby incorporated by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The instant application contains a Sequence Listing which has been submitted in ASCII format via EFS-Web and is hereby incorporated by reference in its entirety. The ASCII copy, created on Apr. 15, 2013, is named 19240.762US3_SL.txt and is 1,833 bytes in size.

BACKGROUND

Chronic kidney disease (CKD), also known as chronic renal disease, is characterized by slow progressive loss of kidney function. Unlike acute kidney disease which may be reversible, CKD irreversibly progresses through five stages (Stages 1-5) of deteriorating kidney function. Stage 1 is slightly diminished kidney function. Gradual, permanent destruction of kidney tissue eventually leads to Stage 5 CKD, also called end-stage renal disease (ESRD), chronic kidney failure (CKF) or chronic renal failure (CRF), which requires kidney replacement therapies such as dialysis or transplantation, and ultimately leads to death.

CKD is a major worldwide public health problem. According to the National Kidney Foundation, 20 million Americans, or one in nine adults in the U.S., have CKD and another 20 million more are at increased risk of developing CKD. In the U.S., there is a rising incidence and prevalence of kidney failure. The number of patients enrolled in the ESRD Medicare-funded program has increased from approximately 10,000 beneficiaries in 1973 to 472,099 as of 2004. While recent trends show that the rate of increase of new cases has progressively flattened, the projected number of ESRD patients by the year 2010 has been estimated to be 651,330. Early detection of CKD is critical in order to prevent or delay progression of CKD, and to provide proper treatment to CKD patients.

SUMMARY

A method is provided for determining whether a subject has chronic kidney disease, the method comprising detecting a protein complex, or one or more components thereof, in a sample from a subject, wherein the protein complex comprises neutrophil gelatinase-associated lipocalin (Ngal), and wherein the size of the protein complex is from about 75 kDa to about 350 kDa.

A method is provided for determining whether a subject with kidney disease has chronic kidney disease or acute kidney disease, the method comprising detecting a protein complex, or one or more components thereof, in a sample from a subject, wherein the protein complex comprises neutrophil gelatinase-associated lipocalin (Ngal), and wherein the size of the protein complex is from about 75 kDa to about 350 kDa, and wherein detection of the protein complex indicates that the subject has chronic kidney disease. The methods can be used to differentiate between chronic kidney disease and acute kidney injury or disease.

A method is provided for determining the efficacy of a therapy to treat chronic kidney disease in a subject, the method comprising detecting a protein complex, or one or more components thereof, in a sample from a subject, wherein the protein complex comprises neutrophil gelatinase-associated lipocalin (Ngal), and wherein the size of the protein complex is from about 75 kDa to about 350 kDa, and wherein detection of the protein complex indicates that the subject should continue receiving the therapy.

In one embodiment, the complex further comprises polymeric immunoglobulin receptor. In one embodiment, the complex further comprises alpha-2-macroglobulin. In one embodiment, the complex further comprises immunoglobulin heavy chain. In one embodiment, the complex further comprises polymeric immunoglobulin receptor, alpha-2-macroglobulin, immunoglobulin heavy chain, or any combination thereof. In one embodiment, the complex does not comprise matrix metalloproteinase-9 (MMP-9). In one embodiment, the complex consists essentially of Ngal, polymeric immunoglobulin receptor, alpha-2-macroglobulin and immunoglobulin heavy chain. In one embodiment, the complex consists of Ngal, polymeric immunoglobulin receptor, alpha-2-macroglobulin and immunoglobulin heavy chain.

In one embodiment, the detecting comprises detecting uncomplexed Ngal, uncomplexed polymeric immunoglobulin receptor, uncomplexed alpha-2-macroglobulin, uncomplexed immunoglobulin heavy chain, or any combination thereof. In one embodiment, the detecting comprises detecting a complex comprising, consisting of, or consisting essentially of Ngal and one or more proteins selected from the group consisting of: polymeric immunoglobulin receptor, alpha-2-macroglobulin, and immunoglobulin heavy chain. In one embodiment, the detecting comprises using an antibody, or fragment thereof. In another embodiment, the antibody comprises a detectable label. In another embodiment, the antibody, or fragment thereof, specifically binds Ngal, polymeric immunoglobulin receptor, alpha-2-macroglobulin or immunoglobulin heavy chain.

In one embodiment, the sample comprises a bodily fluid. In another embodiment, the bodily fluid is urine.

In one embodiment, the chronic kidney disease comprises Alport syndrome, analgesic nephropathy, glomerulonephritis, kidney stones, infection, obstructive uropathy, prostate disease, polycystic kidney disease, reflux nephropathy, diabetic nephropathy, hypertension nephrosclerosis, chronic interstitial nephritis, hypertension, heart disease, diabetes, immune system diseases, lupus, tumors, renal vascular abnormalities, renal artery stenosis, vasculitis, hereditary diseases of the kidney, or any combination thereof.

A method is provided for determining whether a subject has chronic kidney disease, the method comprising: (a) obtaining a sample from a subject; (b) separating the sample into a high molecular weight fraction and a low molecular weight fraction, wherein the high molecular weight fraction comprises proteins of at least about 75 kDa; and (c) detecting an amount of neutrophil gelatinase-associated lipocalin (Ngal) in the high molecular weight fraction; wherein detection of Ngal indicates that the subject has chronic kidney disease. In one embodiment, the amount is a concentration value. In one embodiment, the detecting comprises using an antibody, or fragment thereof. In another embodiment, the antibody, or fragment thereof, specifically binds to Ngal. In one embodiment, the separating comprises using a molecular weight cutoff filter or a molecular weight cutoff membrane.

In one embodiment, the method further comprises: (d) comparing the amount in (c) with a predetermined cutoff value, wherein an amount above the cutoff value indicates that the subject has chronic kidney disease.

In one embodiment, the method further comprises: (d) detecting an amount of Ngal in the low molecular weight fraction; and (e) determining a ratio of the amount of Ngal in the high molecular weight fraction compared to the amount of Ngal in the low molecular weight fraction; wherein a ratio greater than 1 indicates that the subject has chronic kidney disease.

In one embodiment, the detecting comprises an enzyme-linked immunosorbent assay (ELISA). In one embodiment, the high molecular weight fraction comprises a protein complex comprising Ngal, and wherein the size of the protein complex is from about 75 kDa to about 350 kDa. In another embodiment, the high molecular weight fraction comprises a protein complex comprising Ngal, and wherein the size of the protein complex is about 350 kDa.

The invention provides a high molecular weight Ngal composition comprising neutrophil gelatinase-associated lipocalin (Ngal), wherein the size of the protein complex is from about 75 kDa to about 350 kDa. In one embodiment, the composition further comprises polymeric immunoglobulin receptor, alpha-2-macroglobulin, immunoglobulin heavy chain, or any combination thereof. In another embodiment, the composition comprises, consists of, or consists essentially of Ngal and one or more proteins selected from the group consisting of polymeric immunoglobulin receptor, alpha-2-macroglobulin and immunoglobulin heavy chain.

DETAILED DESCRIPTION

Figure 1:
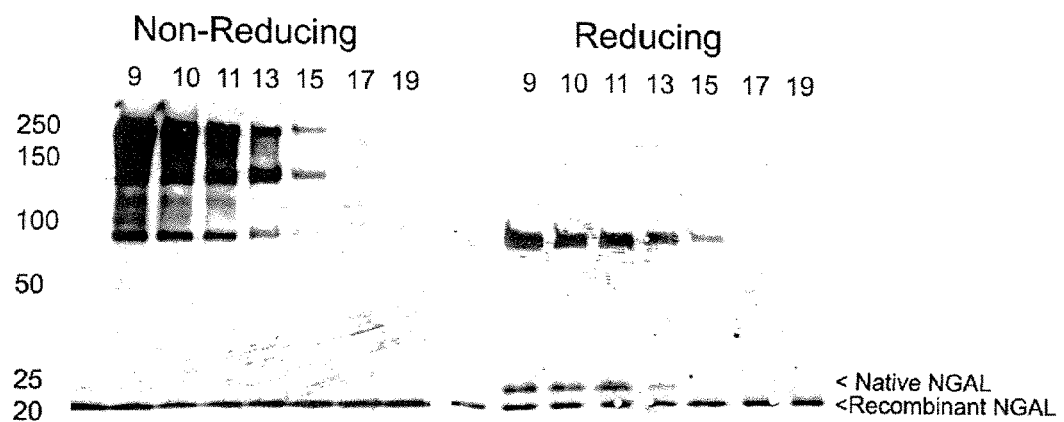
FIG. 1: High molecular weight Ngal immunoreactivity in fractionated urine sample from patient on dialysis. See Example 1.

Diagnosis and clinical follow-up of chronic kidney disease (CKD) are limited by the lack of reliable biomarkers that allow rapid analysis of renal function and damage. The existing diagnostic methods are elaborate and inaccurate. Disclosed herein is a newly identified biomarker which displays elevated levels in CKD and distinguishes between chronic and acute kidney damage.

There is an ongoing, worldwide epidemic of CKD that over the next decade will double the incidence and prevalence of end-stage renal disease (ESRD). This demographic shift will cause a tremendous increase in the number of patients with ESRD, CKD related complications and excess mortality (1).

Early detection of CKD and aggressive treatment of its most potent risk factors, diabetes, hypertension and proteinuria, can decrease the rate of progression of CKD to ESRD.

Kidney biopsy is the gold standard for diagnosis of chronic kidney disease (CKD); however, it is an invasive and expensive procedure. Novel biomarkers of kidney injury have emerged and can be correlated with kidney function. Current clinically used biomarkers of CKD progression are limited in their ability to accurately predict kidney function decline. Serum creatinine, a surrogate for glomerular filtration rate (GFR), is influenced by muscle mass, gender, race, and medications and may fall in advanced CKD secondary to extrarenal clearance (6, 7). Proteinuria, a good predictor of CKD progression; (8-12) is not present in many types of CKD (13). Kidney biopsy can predict the likelihood of progression to ESRD, regardless of the etiology of CKD. Nephron loss results in worsening kidney function through progressive interstitial fibrosis (IF) and tubular atrophy (TA) (14, 15). Furthermore, the degree of tubulointerstitial (TI) alteration on biopsy is more highly correlated with kidney function decline than severity of glomerular damage (16-25). However, kidney biopsy is an invasive procedure and impractical for routine clinical use in the monitoring of CKD progression. Therefore, in order to improve early detection of patients with CKD who will benefit from more aggressive CKD treatment, it is extraordinarily important to evaluate non-invasive biomarkers of CKD progression that are correlated to TI alteration on kidney biopsy (2, 3) (4, 5).

NGAL is a 25 kD lipocalin protein produced by the nephron in response to tubular epithelial damage (26). It has been well established that urine NGAL (uNGAL) levels rise in acute kidney injury (AKI) (27-30). Recent evidence suggest that uNGAL is elevated in CKD, regardless of etiologies, and that elevated uNGAL levels can predict CKD progression (31, 32).

The invention provides a high molecular weight (HMW) form of neutrophil gelatinase-associated lipocalin (Ngal, used interchangeably herein with NGAL) and uses thereof as a biomarker for chronic kidney disease (CKD). A quantitative correlation was found between the presence of a high molecular weight Ngal complex in samples from patients with CKD (see Examples). Methods are provided for detecting a HMW Ngal composition to diagnose CKD in a subject or to determine the efficacy of treatment in a subject receiving treatment for CKD.

The invention provides a novel biomarker for CKD. The biomarker is a high molecular weight form of Ngal. High molecular weight Ngal composition comprises Ngal and has a molecular weight or size of from about 75 kDa to about 350 kDa. In one embodiment, the complex further comprises polymeric immunoglobulin receptor, alpha-2-macroglobulin, immunoglobulin heavy chain, or any combination thereof. As described in Table 1A in the Examples, polymeric immunoglobulin receptor has a molecular weight of about 83 kDa, alpha-2-macroglobulin has a molecular weight of about 163 kDa, and immunoglobulin heavy chain has a molecular weight of about 45 kDa. In another embodiment, the HMW Ngal composition comprises, consists of, or consists essentially of Ngal and one or more proteins selected from the group consisting of polymeric immunoglobulin receptor, alpha-2-macroglobulin and immunoglobulin heavy chain. HMW Ngal may comprise a protein complex between Ngal and polymeric immunoglobulin receptor, alpha-2-macroglobulin, immunoglobulin heavy chain, or any combination thereof as components of the complex. The components of a HMW Ngal complex may be held together covalently or non-covalently or both. One or more of the components of the complex may comprise post-translation protein modification (for example, phosphorylation or glycosylation), where the component was modified before or after formation of the complex.

Ngal is generated when there is a change in renal function due to acute renal injury. Ngal was identified as a reproducible marker that is upregulated after acute kidney damage such as post-transplant rejection, ischemic injury, drug nephrotoxicity. This allows for easy diagnosis and clinical follow-up. See, for example, Schmidt-Ott K M et al. (2007) Dual action of neutrophil gelatinase-associated lipocalin. J Am Soc Nephrol. 18:407-13; Mori K and Nakao K. (2007) Neutrophil gelatinase-associated lipocalin as the real-time indicator of active kidney damage. Kidney International 71:967-970; Wagener G et al. (2008) Increased incidence of acute kidney injury with aprotinin use during cardiac surgery detected with urinary NGAL. Am J Nephrol. 28:576-582. Ngal has also been shown to be a marker of CKD in children (Mitsnefes M M et al. (2006) Serum neutrophil gelatinase-associated lipocalin as a marker of renal function in children with chronic kidney disease. Pediatr Nephrol. 22:101-8).

Two examples of measures of renal function that are currently used to diagnose and classify CKD are (1) albuminurea (albumin found in the urine) and (2) estimates of glomerular filtration rate (GFR). If the kidney fails, albumin and other proteins will leak into the urine while it normally is retained by the body. The GFR is the total volume of plasma filtered by the kidneys. This can be calculated precisely by injecting tracers and following their excretion. Since method is cumbersome, endogenous markers (e.g. creatinine) are used to estimate GFR (estimated GFR=eGFR). These methods based on albuminurea and eGFR have at least the following major disadvantages: (i) they are inaccurate, especially in late disease stages and specific patient populations (children, unusual muscle or fat mass, pregnant women and specific ethnic groups); (ii) eGFR often requires 24 hour urine collection; (iii) creatinine levels (required to estimate GFR) can be falsely elevated; and (iv) these tests do not distinguish between acute and chronic kidney damage.

C reactive protein (CRP) has emerged as an early marker of renal dysfunction. CRP however is a very aspecific marker that will be increased in all forms of infection. Homocysteine, asymmetric dimethyl arginine, brain natriuretic peptide and troponin T are all studied but their value in CDK still requires clinical support form specifically designed intervention studies. However, these markers are also up-regulated in other disease (e.g. cardiovascular).

As described herein, HMW Ngal can be used as a biomarker for CKD in at least four non-limiting applications: (1) as a screening tool to detect preclinical renal failure in the general population and risk groups; (2) as a diagnostic tool to follow disease progression in CKD patients; (3) to determine efficacy of CKD treatment; and (4) as a prognostic tool to determine the type or stage of CKD. If the up-regulation of this high molecular weight form plays a role in the origin or progression of renal failure, therapeutic approaches based on this molecule and its biology may be useful in the treatment of CKD.

Early detection of CKD is important and allows for early commencement of proper therapies to slow the progression of kidney deterioration. Early detection is particularly important in patients who are at high risk of developing CKD. Examples of high risk groups that may be screened for early detection of CKD include patients with a history of diabetes, hypertension, cardiovascular disease, smoking, obesity, nephrotoxic drugs, malignancy, or family history of CKD.

The present discovery is based on the observation of a correlation between CKD and a HMW form of Ngal. The HMW form of Ngal is at least 75 kDa, at least 150 kDa, or at least 350 kDa, and comprises non-Ngal proteins, such as polymeric immunoglobulin receptor, alpha-2-macroglobulin and immunoglobulin heavy chain. In one embodiment, the HMW form of Ngal is about 350 kDa. The HMW form of Ngal may be a large protein complex that comprises component complexes, for example, (i) Ngal bound to polymeric immunoglobulin receptor; (ii) Ngal bound to alpha-2-macroglobulin; (iii) Ngal bound to immunoglobulin heavy chain; (iv) Ngal bound to polymeric immunoglobulin receptor and alpha-2-macroglobulin; (v) Ngal bound to polymeric immunoglobulin receptor and immunoglobulin heavy chain; (vi) Ngal bound to alpha-2-macroglobulin and immunoglobulin heavy chain; (vii) Ngal bound to polymeric immunoglobulin receptor, alpha-2-macroglobulin and immunoglobulin heavy chain. In embodiments of the methods provided herein, any one or more component complexes may be detected to assess the presence of HMW Ngal in a sample. In other embodiments, individual uncomplexed protein components of HMW Ngal may be detected to assess the presence of HMW Ngal in a sample. For example, uncomplexed or free Ngal, polymeric immunoglobulin receptor, alpha-2-macroglobulin, immunoglobulin heavy chain, or any combination thereof.

A 125 kDa complex between Ngal and matrix metalloproteinase-9 (MMP-9) has been previously reported (U.S. Pat. No. 7,153,660; Yan L et al. (2001) The high molecular weight urinary matrix metalloproteinase (MMP) activity is a complex of gelatinase B/MMP-9 and neutrophil gelatinase-associated lipocalin (NGAL)).

Methods are provided for determining an amount of HMW Ngal in a sample. For example, a patient sample can be subjected to a molecular weight filter to separate a high molecular weight fraction of the sample (comprising any HMW Ngal present in the sample) and a low molecular weight fraction. Separating the fractions will separate any HMW Ngal away from any uncomplexed or free Ngal in the sample, thus eliminating potential cross-detection between HMW Ngal and uncomplexed or free Ngal. To determine the presence of HMW Ngal in the sample, protein detection methods known in the art can be used to detect the Ngal complex, component complexes thereof, or individual protein components of the complex. For example, antibody detection of Ngal can be used, for example, enzyme-linked immunosorbent assay (ELISA). Antibodies that specifically bind Ngal are available from commercial vendors, such as Santa Cruz Biotechnology. Ngal ELISA kits are available from commercial vendors, such as R&D Systems and Bio-Proto.

EXAMPLES

Example 1

NGAL Immunoreactivity is Found at Different Molecular Weights

Urine from a patient on dialysis was fractionated on an anion exchange column in Buffer (MES 20 mM, pH 6.0) and salt eluted (Buffer A+NaCl, 0.5M). As shown in FIG. 1, fractions were immunoblotted for NGAL and high molecular weight immunoreactivity was identified in early fractions from the column. The same samples were then reduced with beta-mercaptoethanol resulting in dissolution of the high molecular weight complexes and the appearance of 'monomeric' glycosylated NGAL at 25 KDa. Recombinant NGAL was added to the gel as an internal maker (21 KDa). Note that monomeric NGAL might derive from any of the high molecular bands.

Figure 2:
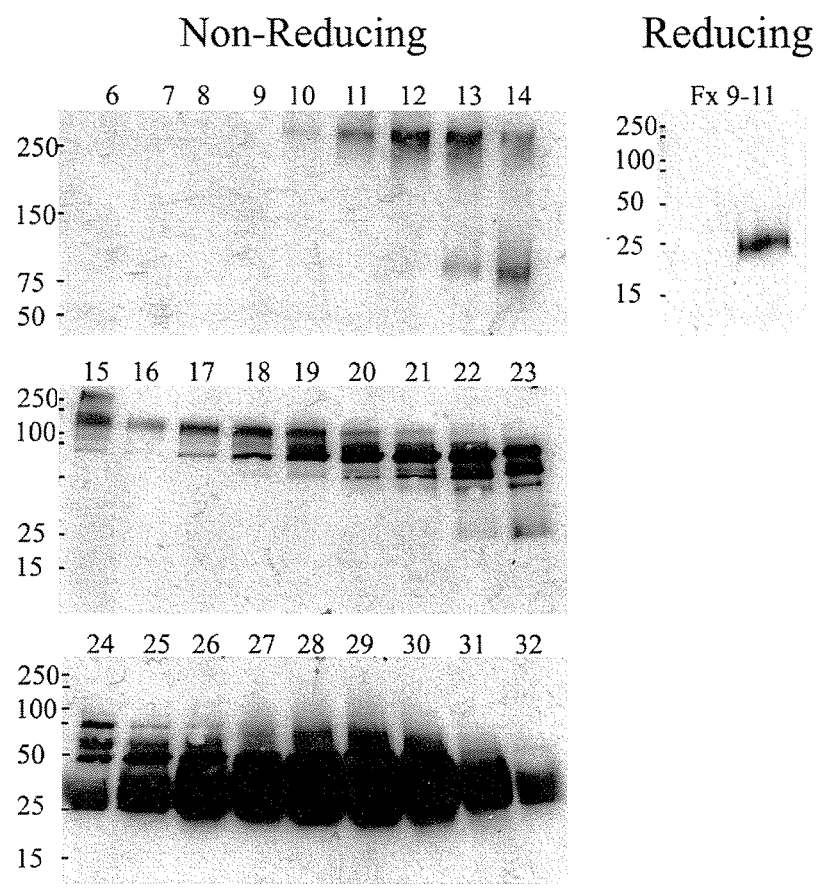
FIG. 2: Different HMW Ngal compositions are found in different sample fractions. See Example 1.

NGAL complexes were isolated first by anion exchange chromatography (Buffer system=MES 20 mM pH 6.0—see above) and fractions containing high molecular weight NGAL immunoreacitvity were pooled and then further fractionated by gel filtration by Superdex200 (see FIG. 2). A number of molecular weights were found on non-reducing gels including 350, 125, 75, 37, 25 KDa, and these forms were located in different fractions. Fractions 9-12 had only the 350 KDa reactive band. This fraction was pooled and then reduced. After reduction, the only immunoreactive molecule was 25 KDa NGAL. These data show that NGAL was associated with proteins totaling 350 KDa. The 350 KDa band was sequenced (see Example 2).

Example 2

Identification of Proteins in High Molecular Weight NGAL Complex

Samples of a HMW Ngal composition (350 kDa) were subjected to tryptic digest. To obtain a mass fingerprint of the proteins in the sample, 100% of the peptides generated by the digest were subjected to a micro-clean-up procedure using 2 µl bed-volume of Poros 50 R2 (PerSpective Biosystems) reversed-phase (RP) beads, packed in an Eppendorf gel-loading tip. Mass spectrometry (MALDI-ReTOF) was conducted on two peptide pools (16 and 30% MeCN) recovered from the RP-microtip column using a Bruker Ultraflex TOF/TOF instrument with delayed extraction.

For peptide mass fingerprinting (PMF), experimental masses (m/z) combined from both MALDI-ReTOF experiments were used to search a non-redundant human protein database (NR; ~148,041 entries), using the PeptideSearch (M. Mann, Max-Planck Institute for Biochemistry, Martinsried 82152, Germany) algorithm. A molecular weight range twice the predicted weight was covered, with a mass accuracy restriction better than 40 ppm, and maximum one missed cleavage site allowed per peptide.

Mass spectrometric sequencing (MALDI-TOF-MS/MS) of selected peptides from the partially fractionated pools was done on a Bruker Ultrflex TOF/TOF instrument in 'Lift' mode, and the fragment ion spectra taken to search human databases using the MASCOT MS/MS Ion Search program (Matrix Science).

The experiment described above identified the following proteins in the sample of HMW Ngal: polymeric immunoglobulin receptor, alpha-2-macroglobulin and immunoglobulin heavy chain (see Table 1A).

TABLE 1A

Proteins identified as components of a HMW form of Ngal

| Name | Size | NCBI # | Sequence |
|---|---|---|---|
| Polymeric immunoglobulin receptor | ~83 kDa | 31377806 | LVSLTLNLVTR; (SEQ ID NO: 1) ILLNPQDKDGSFSVVITGLR; (SEQ ID NO: 2) QGHFYGETAAVYVAVEER; (SEQ ID NO: 3) |

TABLE 1A-continued

Proteins identified as components of a HMW form of Ngal

| Name | Size | NCBI # | Sequence |
|---|---|---|---|
| α-2-macroglobulin | ~163 kDa | 25303946 | HYDGSYSTFGER; (SEQ ID NO: 4) QGIPFFGQVR; (SEQ ID NO: 5) |
| Immunoglobulin heavy chain | ~45 kDa | 9367869 | WLQGSQELPR; (SEQ ID NO: 6) YLTWASR; (SEQ ID NO: 7) QEPSQGTTTFAVTSILR; (SEQ ID NO: 8) |

Example 3

Patterns of High Molecular Weight NGAL in Patient Populations

Figure 3:
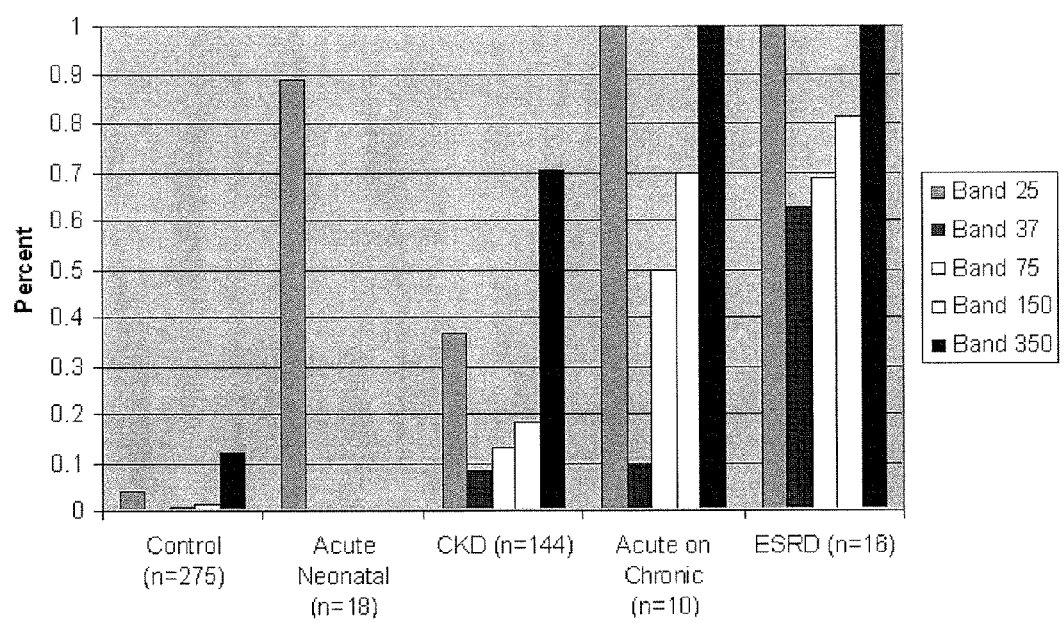
FIG. 3: Patterns of Ngal in different patient populations. See Example 3.

NGAL Western Blots from four previous clinical studies were analyzed for the presence of HMW NGAL. Results are shown in FIG. 3; patients were grouped according to renal diagnosis as follows:
1. Those patients who displayed stable eGFR >60 ml/min were labeled "Controls".
2. Very Low Birthweight Infants (<1500 grams) who attained a clinical diagnosis of Acute Renal Failure were labeled "Acute Neonatal".
3. Patients with baseline eGFR <60 ml/min that was stable either over 3 day hospital stay or stable over 3 months were denoted "CKD".
4. Patients who demonstrated a baseline eGFR <60 ml/min and who demonstrated either a new-onset and sustained 1.5× increase in creatinine or a new onset and sustained 25% decrease in eGFR (satisfying minimal RIFLE (risk for kidney dysfunction, injury to the kidney, failure of kidney function, loss of kidney function, and end-stage kidney disease) criteria) over the course of hospitalization were denoted "Acute on Chronic".
5. Patients with dialysis dependence prior to urine sampling were labeled "ESRD".

As shown in FIG. 3, high molecular weight forms of NGAL correlate with different types of CKD.

Example 4

Prospective Cohort Study to Determine the Relationship Between Novel Biomarkers and Kidney Biopsy Findings in a Broad Spectrum Of Patients with CKD, Including Primary and Secondary Glomerular, Tubulointerstitial (TI), and Vascular Diseases This example presents results of a biopsy cohort of patients with CKD from a spectrum of etiologies. This study includes the important discovery of a high molecular weight (HMW) NGAL complex that can be measured by ELISA. HMW NGAL accounted for a small proportion of total NGAL measured. The results (described below) also show that uNGAL levels are elevated in the setting of severe TI damage and when glomerular injury is co-prevalent with TI damage. A strong inverse correlation between GFR and uNGAL is also demonstrated by both ELISA and Western Blot and a weak correlation between proteinuria and uNGAL measured by ELISA. Some differences were found in uNGAL measurements based on the type of NGAL assay used, but the relationships between uNGAL and either biopsy findings or GFR were not altered.

uNGAL accurately discriminates AKI from stable CKD (27), suggesting that non-progressive CKD does not induce tubular production of NGAL to the same extent as AKI. However, multiple studies have demonstrated that uNGAL is a marker of CKD severity and progression (34, 35, 32, 36, 31, 37). Furthermore, the fractional urinary excretion of NGAL is increased in the setting of CKD, suggesting active tubular production in response to ongoing tubular injury (36). A renal tubular source of uNGAL was confirmed by immunohistochemical staining in Lee grade III IgA nephropathy patients (32). These observations, and the results of this study, suggest that in the setting of CKD, uNGAL represents a marker of the degree of onging, active kidney damage, as proposed by Mori and Nakao (37).

While the sample size of this study was small and individual primary etiologies of CKD were not evaluated, histological characteristics associated with NGAL expression were found that were independent of underlying disease. Furthermore, the inclusion of patients with comorbidities makes these results generalizable. Since there was no long-term follow-up data for patients, uNGAL values could not be correlated with disease progression. Larger scale studies with long follow-up periods can be conducted.

As shown below, NGAL, a well-established marker of AKI, is elevated in patients with TI damage on kidney biopsy. uNGAL is elevated in patients with severe TA and IF, known predictors of progressive disease. Measurement of uNGAL may be a non-invasive way to gain insight into pathophysiologic changes within the kidney and help identify patients who are will progress to end stage disease.

Results

Figure 4:
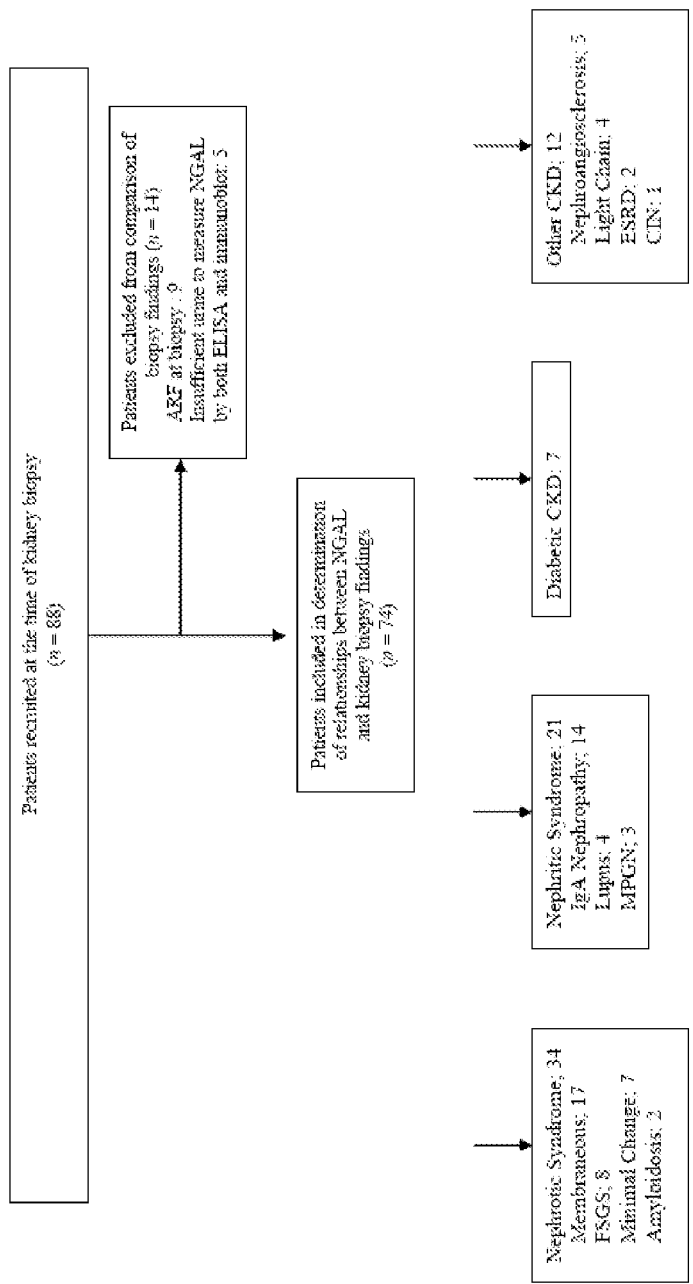
FIG. 4: Patient cohort study described in Example 4.

Of 88 patients who underwent kidney biopsy, 14 were excluded for reasons indicated in FIG. 4. Of the remaining 74 patients, 78% were male and mean age was 51.5 years (SD, 17.2). Diagnostic groups based on histology are presented in FIG. 4. uNGAL, measured by immunoblot or ELISA, was not significantly different among these groups (Table 1B).

An inverse relationship was found between uNGAL and GFR ($r=-0.605$, $p<0.001$ and $r=-0.491$, $p<0.001$ for Immunoblot and ELISA, respectively.) Although there was no significant correlation between proteinuria and uNGAL when measured by immunoblot ($r=0.222$ $p=0.06$), we identified a weak, statistically significant relationship between ELISA and proteinuria, ($r=0.297$, $p=0.01$), accounting for approximately 7% of the variability in the ELISA measurement.

In the determination of high molecular weight forms of NGAL, 10 samples were excluded because insufficient urine volume remained, 18 were excluded because NGAL loss (described below) was >50% of the total value measured by ELISA. 48 patients had measurement of NGAL in the filtrate (MW<100 kDa) and retentate (MW>100 kDa). A higher molecular weight NGAL complex was found in the retentate that could be measured by ELISA. Analysis of the amount of NGAL in the retentate revealed that high molecular weight forms accounted for a mean 3.8%, SD 7.7%, range (0-41.9%) of the entire NGAL measurement.

Methods

Patients: Patients were 18 years and older undergoing kidney biopsy at the University of Parma as part of routine care from January 2005-April 2008. Urine and fasting blood samples were collected at the time of biopsy. Patients were excluded if kidney biopsy findings were consistent with AKI or if insufficient urine volume was collected to perform both biomarker assays. At the time of biopsy routine clinical and laboratory information were obtained (see Table 3).

TABLE 3

Baseline characteristics

| Parameter | All Patients Mean (SD) |
|---|---|
| Gender (% female) | 32.4 |
| Age | 51.5 (17.2) |
| Systolic BP (mmHg) | 139 (22.5) |
| Diastolic BP (mmHg) | 82 (11.1) |
| Diabetes (%) | 16.2 |
| Hypertension (%) | 71.6 |

TABLE 1B

Mean uNGAL, GFR and Proteinuria Among Diagnostic Groups of CKD

| Diagnostic Group | Mean uNGAL western (SD) | P-value | Mean uNGAL ELISA (SD) | P-value | Mean GFR (SD) | P-Value | Mean Proteinuria (SD) | P-value |
|---|---|---|---|---|---|---|---|---|
| Nephrotic (n = 34) | 89 (213) | 0.381 | 109 (179) | 0.110 | 58 (31) | 0.041 | 7.6 (6.4) | <0.001 |
| Nephritic (n = 21) | 36 (76) | | 33 (52) | | 63 (31) | | 7.2 (4.0) | |
| Diabetic (n = 7) | 80 (95) | | 367 (745) | | 53 (31) | | 2.7 (1.9) | |
| Other (n = 12) | 81 (106) | | 133 (214) | | 38 (33) | | 3.1 (2.6) | |

TI damage was defined as the degree of TA or IF on biopsy. Patients with severe TI damage had uNGAL levels that were significantly 3-5 fold greater than for those patients with mild degrees of TI damage (Table 2A). uNGAL levels were also significantly greater for those patients with global glomerulosclerosis (Table 2B). It is interesting to note that in these 51 patients with global glomerulosclerosis all had some degree of TA with 39% having severe TA. Furthermore, 50 of these patients with global glomerulosclerosis had some degree of IF, with 38% having severe IF. GFR was significantly lower in patients with severe TI damage and global glomerulosclerosis (Tables 2A and 2B). Proteinuria levels were not associated with any biopsy findings.

TABLE 3-continued

Baseline characteristics

| Parameter | All Patients Mean (SD) |
|---|---|
| GFR(mL/min/1.73 m2) | 55.9 (31.7) |
| Serum Creatinine (mg/dl) | 1.86 (1.24) |
| Proteinuria (g/24 h) | 5.46 (5.21) |
| Serum Protein (g/dl) | 5.44 (1.29) |
| Albumin (g/dl) | 1.86 (1.24) |
| Cholesterol (mg/dl) | 248 (71.4) |
| uNGAL Elisa (µg/g creatinine) | 115 (275) |
| uNGAL Western (µg/g creatinine) | 71.6 (158) |

TABLE 3-continued

Baseline characteristics

| Parameter | All Patients Mean (SD) |
|---|---|
| Diagnostic Categories | |
| Nephrotic (%) | 45.9 |
| Nephritic (%) | 28.4 |
| Diabetic (%) | 9.5 |
| Other (%) | 16.2 |

1. N = 67 2. N = 64 3. N = 62

GFR was estimated using the MDRD formula (33). Participants were 74 Caucasian patients undergoing kidney biopsy as a part of routine care. 78% were men, 46% nephrotic syndrome, 14% nephritic syndrome, 10% diabetic CKD, 16% other. Diagnosis of CKD was based on the consensus definition developed by the Kidney Disease Outcomes Quality Initiative and assigned by researchers who were blinded to experimental measurements. Kidney biopsy scores for individual pathologic findings were determined by two blinded pathologists. An activity and chronicity index were calculated. Kidney function was evaluated by serum creatinine measurement, glomerular filtration rate (GFR) calculation and 24-hour urine protein measurement, other routine serum chemistries were measured (see below). Urinary NGAL was measured by immunoblot and enzyme-linked immunesorbent assay, urine creatinine by spectrophotometry, and serum creatinine by Jaffe kinetic reaction (see below). Experimental measurements were not available to treating physicians.

Urine Ngal measurements: 1 mL of urine was centrifuged at 12,000 rpm for 10 minutes and stored it at −80° C. uNGAL (10 uL) was quantified by immunoblots with nonreducing 4% to 15% gradient polyacrylamide gels (Bio-Rad Laboratories) and monoclonal antibodies (1:1000; Antibody Shop, BioPorto Diagnostics) with standards (0.2 to 10 ng) of human recombinant NGAL protein (32, 33). The measurement was reproducible to 0.4 ng/lane. The immunoblotting procedure was selected to authenticate monomeric NGAL at 25 kD. Urinary NGAL was also measured using enzyme-linked immunosorbant assay (ELISA) (Architect, Abbott).

HMW Ngal measurements: To determine the potential contribution of high molecular weight NGAL complexes that may be derived from the serum to the ELISA measurement, 400 ul of urine was filtered with a Microcon Ultracel YM-100 100 kDa filter (Millipore Corporation) and centrifuged until nearly dry. PBS was added to the retentate to bring the volume to a minimum of 100 ul. Total volumes were determined and NGAL was measured in the original sample, the flow through and retentate using the Abbott Architect NGAL Assay. NGAL loss was calculated by subtracting the amount of NGAL measured in the flow through and retentate from the total NGAL concentration.

Creatinine measurements: Urinary creatinine was measured by using a QuantiChrom Creatinine Assay Kit (BioAssay Systems). Serum creatinine was measured by Jaffe reaction. Urine protein was measured by nephelometry.

Histological evaluation: Formalin-fixed tissues were embedded in paraffin, sectioned and stained with hematoxylin/eosin, sliver methenamine and periodic-acid Schiff. IgG, IgM, IgA, C3 and fibrinogen deposition were detected by immunoflourescence staining Glomerular and mesangial proliferation were graded from 0-3. Grade 0, 1, 2, 3 represented normal, <1/3, 1/3-2/3, >2/3 of the glomerulus involved respectively. TI lesions were also scored as 0, absent; 1, mild; 2, moderate; 3, severe.

Statistical analysis: Statistical analysis was performed with SPSS v16.0 (SPSS, Chicago, Ill.). Continuous variables were log-transformed and compared by Student's t-test for unequal variances or ANOVA. Categorical variables were compared by $c^2$. The null hypothesis was rejected at p<0.05. Data were represented as the mean±standard deviation (SD). Pearson Correlations were run between urine NGAL and proteinuria, urine NGAL and GFR to determine if a linear relationship existed.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

TABLE 2A

Tabulointerstitial Findings and mean uNGAL, proteinuria and GFR

| | Number of Patients | Mean uNGAL western (SD) (µ/g creatinine) | | | P value | Mean uNGAL ELISA (SD) (µg/g creatinine) | | | P value |
|---|---|---|---|---|---|---|---|---|---|
| Interstitial Monocellular Infiltration | 45 | 23 (46) | | 103 (194) | 0.005 | 55 (134) | | 154 (332) | 0.048 |
| Atherosclerosis | Present 63 | Absent 14 (18) | | Present 52 (170) | 0.030 | Absent 36 (72) | | Present 129 (295) | 0.064 |
| Interstitial Fibrosis | Absent: 7 Mild: 44 Severe: 24 | Absent 48 (91) | Mild 30 (52) | -Severe‡ 159 (245) | <0.001 | Absent 141 (253) | Mild 51 (104) | Severe- 231 (435) | 0.018 |
| Tubular Atrophy | Absent: 3 Mild: 47 Severe: 24 | Absent 8 (11) | Mild 31 (65) | Severe)‡ 159 (244 | <0.001 | Absent 20 (14) | Mild 59 (148) | Severe)† 219 (424) | 0.019 |

| | Mean protsinursis (SD) | | P value | Mean GFR (SD) | | P value |
|---|---|---|---|---|---|---|
| Interstitial Monocellular Infiltration | 6.2 (6.3) | 5.0 (4.4) | 0.749 | 73 (31) | 45 (27) | <0.001 |

TABLE 2A-continued

Tabulointerstitial Findings and mean uNGAL, proteinuria and GFR

| | | | | | | | | |
|---|---|---|---|---|---|---|---|---|
| Atherosclerosis | Absent | | Present | 0.717 | Absent | | Present | 0.002 |
| | 5.7 (6.2) | | 5.4 (6.1) | | 75 (36) | | 63 (32) | |
| Interstitial | Absent | Mild | Severe | 0.429 | Absent | Mild | Severe | <0.001 |
| Fibrosis | 8.2 (7.1) | 4.9 (4.7) | 5.7 (5.5) | | 70 (38) | 56 (25) | 32 (25)† | |
| Tubular | Absent | Mild | Severe | 0.754 | Absent | Mild | Severe | <0.001 |
| Atrophy | 5.1 (4.8) | 5.2 (6.1) | 5.9 (5.6) | | 98 (18) | 56 (29)* | 34 (25)‡ | |

†$p < 0.05$,
*$p < 0.01$,
‡$p < 0.001$

Interstitial Mononuclear cell Infiltration and atherosclerosis, were analyzed as either absent (biopsy score 0) or present (biopsy score 1-3).
Interstitial fibrosos and tubular atrophy were analyzed as none = grade 0. mild = grade 1, and severe = grade 2 or 3.

TABLE 2B

Glomerular Findings and Mean uNGAL, proteinuria and GFR

| | Number with biopsy finding present | Mean uNGAL western (SD) (μg/g creatine) | | | Mean uNGAL ELSIA (SD) (xg/g creatinine) | | |
|---|---|---|---|---|---|---|---|
| | | Absent | Present | p-value | Absent | Present | p-value |
| Global Glomerulosclerosis | 51 | 29 (54) | 91 (185) | 0.045 | 57 (149) | 142 (314) | 0.036 |
| Glomerular Leukocyte Infiltration | 8 | 70 (164) | 82 (111) | 0.105 | 122 (290) | 63 (78) | 0.441 |
| Capillary Wall Thrombosis | 28 | 97 (186) | 46 (93) | 0.037 | 128 (318) | 99 (189) | 0.740 |
| Mesangial Cell Proliferation | 17 | 70 (171) | 81 (108) | 0.615 | 122 (289) | 92 (180) | 0.401 |
| Mesangial Matrix Expension | 59 | 45 (58) | 45 (68) | 0.825 | 66 (102) | 128 (303) | 0.673 |
| Cellular Cresents | 12 | 78 (171) | 38 (59) | 0.523 | 93 (163) | 233 (581) | 0.532 |
| Fibrous Cresents | 21 | 56 (149) | 112 (176) | 0.101 | 77 (150) | 213 (452) | 0.256 |

| | Mean proteinurais (SD) | | | Mean GFR (SD) | | |
|---|---|---|---|---|---|---|
| | Absent | Present | p-value | Absent | Present | P-value |
| Global Glomerulosclerosis | 6.8 (8.8) | 4.9 (4.4) | 0.421 | 69 (33) | 50 (29) | 0.037 |
| Glomerular Leukocyte Infiltration | 5.7 (5.4) | 3.9 (3.3) | 0.385 | 57 (33) | 47 (22) | 0.582 |
| Capillary Wall Thrombosis | 5.2 (5.3) | 5.8 (5.2) | 0.478 | 52 (33) | 62 (29) | 0.104 |
| Mesangial Cell Proliferation | 8.0 (5.5) | 3.7 (3.6) | 0.063 | 55 (32) | 60 (30) | 0.219 |
| Mesangial Matrix Expension | 6.2 (5.5) | 5.3 (5.2) | 0.502 | 83 (65) | 54 (31) | 0.584 |
| Cellular Cresents | 4.8 (3.7) | 8.7 (9.5) | 0.587 | 54 (31) | 67 (32) | 0.126 |
| Fibrous Cresents | 5.5 (4.7) | 5.4 (6.4) | 0.493 | 59 (32) | 48 (30) | 0.180 |

All glomerular findings were analyzed as either ansence (grade 0) or presence (grade 1-3)

REFERENCES

1. Gilbertson, D T, Liu, J, Xue, J L, Louis, T A, Solid, C A, Ebben, J P & Collins, A J: Projecting the number of patients with end-stage renal disease in the United States to the year 2015. *J Am Soc Nephrol,* 16: 3736-41, 2005.
2. Peterson, J C, Adler, S, Burkart, J M, Greene, T, Hebert, L A, Hunsicker, L G, King, A J, Klahr, S, Massry, S G & Seifter, J L: Blood pressure control, proteinuria, and the progression of renal disease. The Modification of Diet in Renal Disease Study. *Ann Intern Med,* 123: 754-62, 1995.
3. Saweirs, W W & Goddard, J: What are the best treatments for early chronic kidney disease? A background paper prepared for the UK Consensus Conference on early chronic kidney disease. *Nephrol Dial Transplant,* 22 Suppl 9: ix31-38, 2007.
4. Hunsicker, L G, Adler, S, Caggiula, A, England, B K, Greene, T, Kusek, J W, Rogers, N L & Teschan, P E: Predictors of the progression of renal disease in the Modification of Diet in Renal Disease Study. *Kidney Int,* 51: 1908-19, 1997.
5. de Zeeuw, D, Ramjit, D, Zhang, Z, Ribeiro, A B, Kurokawa, K, Lash, J P, Chan, J, Remuzzi, G, Brenner, B M & Shahinfar, S: Renal risk and renoprotection among ethnic groups with type 2 diabetic nephropathy: a post hoc analysis of RENAAL. *Kidney Int,* 69: 1675-82, 2006.
6. Gaspari, F, Perico, N, Ruggenenti, P, Mosconi, L, Amuchastegui, C S, Guerini, E, Daina, E & Remuzzi, G: Plasma clearance of nonradioactive iohexol as a measure of glomerular filtration rate. *J Am Soc Nephrol,* 6: 257-63, 1995.
7. Perrone, R D, Madias, N E & Levey, A S: Serum creatinine as an index of renal function: new insights into old concepts. *Clin Chem,* 38: 1933-53, 1992.

8. Lewis, E J, Hunsicker, L G, Clarke, W R, Berl, T, Pohl, M A, Lewis, J B, Ritz, E, Atkins, R C, Rohde, R & Raz, I: Renoprotective effect of the angiotensin-receptor antagonist irbesartan in patients with nephropathy due to type 2 diabetes. *N Engl J Med,* 345: 851-60, 2001.
9. Brenner, B M, Cooper, M E, de Zeeuw, D, Keane, W F, Mitch, W E, Parving, H H, Remuzzi, G, Snapinn, S M, Zhang, Z & Shahinfar, S: Effects of losartan on renal and cardiovascular outcomes in patients with type 2 diabetes and nephropathy. *N Engl J Med,* 345: 861-9, 2001.
10. Eddy, A A: Proteinuria and interstitial injury. *Nephrol Dial Transplant,* 19: 277-81, 2004.
11. Eddy, A A, McCulloch, L, Liu, E & Adams, J: A relationship between proteinuria and acute tubulointerstitial disease in rats with experimental nephrotic syndrome. *Am J Pathol,* 138: 1111-23, 1991.
12. Magil, A B: Tubulointerstitial lesions in human membranous glomerulonephritis: relationship to proteinuria. *Am J Kidney Dis,* 25: 375-9, 1995.
13. Remuzzi, G, Ruggenenti, P & Benigni, A: Understanding the nature of renal disease progression. *Kidney Int,* 51: 2-15, 1997.
14. Metcalfe, W: How does early chronic kidney disease progress? A background paper prepared for the UK Consensus Conference on early chronic kidney disease. *Nephrol Dial Transplant,* 22 Suppl 9: ix26-30, 2007.
15. Eddy, A A: Progression in chronic kidney disease. *Adv Chronic Kidney Dis,* 12: 353-65, 2005.
16. Hill, G S, Delahousse, M, Nochy, D, Tomkiewicz, E, Remy, P, Mignon, F & Mery, J P: A new morphologic index for the evaluation of renal biopsies in lupus nephritis. *Kidney Int,* 58: 1160-73, 2000.
17. Risdon, R A, Sloper, J C & De Wardener, H E: Relationship between renal function and histological changes found in renal-biopsy specimens from patients with persistent glomerular nephritis. *Lancet,* 2: 363-6, 1968.
18. Bohle, A, Wehrmann, M, Bogenschutz, O, Batz, C, Muller, C A & Muller, G A: The pathogenesis of chronic renal failure in diabetic nephropathy. Investigation of 488 cases of diabetic glomerulosclerosis. *Pathol Res Pract,* 187: 251-9, 1991.
19. Bogenschutz, O, Bohle, A, Batz, C, Wehrmann, M, Pressler, H, Kendziorra, H & Gartner, H V: IgA nephritis: on the importance of morphological and clinical parameters in the long-term prognosis of 239 patients. *Am J Nephrol,* 10: 137-47, 1990.
20. Vleming, L J, de Fijter, J W, Westendorp, R G, Daha, M R, Bruijn, J A & van Es, L A: Histomorphometric correlates of renal failure in IgA nephropathy. *Clin Nephrol,* 49: 337-44, 1998.
21. Bohle, A, Mackensen-Haen, S & von Gise, H: Significance of tubulointerstitial changes in the renal cortex for the excretory function and concentration ability of the kidney: a morphometric contribution. *Am J Nephrol,* 7: 421-33, 1987.
22. Schmitt, H, Cavalcanti de Oliveira, V & Bohle, A: Tubulointerstitial alterations in type I membranoproliferative glomerulonephritis. An investigation of 259 cases. *Pathol Res Pract,* 182: 6-10, 1987.
23. Mackensen-Haen, S, Bohle, A, Christensen, J, Wehrmann, M, Kendziorra, H & Kokot, F: The consequences for renal function of widening of the interstitium and changes in the tubular epithelium of the renal cortex and outer medulla in various renal diseases. *Clin Nephrol,* 37: 70-7, 1992.
24. Wehrmann, M, Bohle, A, Held, H, Schumm, G, Kendziorra, H & Pressler, H: Long-term prognosis of focal sclerosing glomerulonephritis. An analysis of 250 cases with particular regard to tubulointerstitial changes. *Clin Nephrol,* 33: 115-22, 1990.
25. D'Amico, G, Ferrario, F & Rastaldi, M P: Tubulointerstitial damage in glomerular diseases: its role in the progression of renal damage. *Am J Kidney Dis,* 26: 124-32, 1995.
26. Flo, T H, Smith, K D, Sato, S, Rodriguez, D J, Holmes, M A, Strong, R K, Akira, S & Aderem, A: Lipocalin 2 mediates an innate immune response to bacterial infection by sequestrating iron. *Nature,* 432: 917-21, 2004.
27. Nickolas, T L, O'Rourke, M J, Yang, J, Sise, M E, Canetta, P A, Barasch, N, Buchen, C, Khan, F, Mori, K, Giglio, J, Devarajan, P & Barasch, J: Sensitivity and specificity of a single emergency department measurement of urinary neutrophil gelatinase-associated lipocalin for diagnosing acute kidney injury. *Ann Intern Med,* 148: 810-9, 2008.
28. Mishra, J, Mori, K, Ma, Q, Kelly, C, Barasch, J & Devarajan, P: Neutrophil gelatinase-associated lipocalin: a novel early urinary biomarker for cisplatin nephrotoxicity. *Am J Nephrol,* 24: 307-15, 2004.
29. Mishra, J, Ma, Q, Prada, A, Mitsnefes, M, Zahedi, K, Yang, J, Barasch, J & Devarajan, P: Identification of neutrophil gelatinase-associated lipocalin as a novel early urinary biomarker for ischemic renal injury. *J Am Soc Nephrol,* 14: 2534-43, 2003.
30. Mishra, J, Ma, Q, Kelly, C, Mitsnefes, M, Mori, K, Barasch, J & Devarajan, P: Kidney NGAL is a novel early marker of acute injury following transplantation. *Pediatr Nephrol,* 21: 856-63, 2006.
31. Mitsnefes, M M, Kathman, T S, Mishra, J, Kartal, J, Khoury, P R, Nickolas, TL, Barasch, J & Devarajan, P: Serum neutrophil gelatinase-associated lipocalin as a marker of renal function in children with chronic kidney disease. *Pediatr Nephrol,* 22: 101-8, 2007.
32. Ding, H, He, Y, Li, K, Yang, J, Li, X, Lu, R & Gao, W: Urinary neutrophil gelatinase-associated lipocalin (NGAL) is an early biomarker for renal tubulointerstitial injury in IgA nephropathy. *Clin Immunol,* 123: 227-34, 2007.
33. Levey, A S, Bosch, J P, Lewis, J B, Greene, T, Rogers, N & Roth, D: A more accurate method to estimate glomerular filtration rate from serum creatinine: a new prediction equation. Modification of Diet in Renal Disease Study Group. *Ann Intern Med,* 130: 461-70, 1999.
34. Bolignano, D, Coppolino, G, Campo, S, Aloisi, C, Nicocia, G, Frisina, N & Buemi, M: Urinary neutrophil gelatinase-associated lipocalin (NGAL) is associated with severity of renal disease in proteinuric patients. *Nephrol Dial Transplant,* 23: 414-6, 2008.
35. Bolignano, D, Coppolino, G, Campo, S, Aloisi, C, Nicocia, G, Frisina, N & Buemi, M: Neutrophil gelatinase-associated lipocalin in patients with autosomal-dominant polycystic kidney disease. *Am J Nephrol,* 27: 373-8, 2007.
36. Bolignano, D, Lacquaniti, A, Coppolino, G, Campo, S, Arena, A & Buemi, M: Neutrophil Gelatinase-Associated Lipocalin Reflects the Severity of Renal Impairment in Subjects Affected by Chronic Kidney Disease. *Kidney Blood Press Res,* 31: 255-258, 2008.
37. Mori, K & Nakao, K: Neutrophil gelatinase-associated lipocalin as the real-time indicator of active kidney damage. *Kidney Int,* 71: 967-70, 2007.

What is claimed is:

1. A method for determining whether a subject has chronic kidney disease, the method comprising:
   determining an amount of a protein complex in a urine sample from a subject, wherein the protein complex comprises neutrophil gelatinase-associated lipocalin (Ngal), polymeric immunoglobulin receptor, alpha-2-macroglobulin, and immunoglobulin heavy chain; and wherein the size of the protein complex is about 350 kDa;
   comparing the amount of the protein complex in the sample with a predetermined cutoff value; and
   diagnosing the subject as having chronic kidney disease when the amount of the protein complex in the urine sample is above the predetermined cutoff value.

2. The method of claim 1, wherein the determining comprises using an antibody, or binding fragment thereof.

3. The method of claim 2, wherein the antibody comprises a detectable label.

4. The method of claim 2, wherein the antibody, or binding fragment thereof, specifically binds to Ngal, polymeric immunoglobulin receptor, alpha-2-macroglobulin or immunoglobulin heavy chain.

* * * * *

UNITED STATES PATENT AND TRADEMARK OFFICE
CERTIFICATE OF CORRECTION

PATENT NO. : 8,592,170 B2  Page 1 of 1
APPLICATION NO. : 12/922047
DATED : November 26, 2013
INVENTOR(S) : Barasch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 347 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 8

<210> SEQ ID NO 1
<211> LENGTH: 11
<212> TYPE: PRT
<213> ORGANISM: Homo sapiens

<400> SEQUENCE: 1

Leu Val Ser Leu Thr Leu Asn Leu Val Thr Arg
1               5                   10

<210> SEQ ID NO 2
<211> LENGTH: 20
<212> TYPE: PRT
<213> ORGANISM: Homo sapiens

<400> SEQUENCE: 2

Ile Leu Leu Asn Pro Gln Asp Lys Asp Gly Ser Phe Ser Val Val Ile
1               5                   10                  15

Thr Gly Leu Arg
            20

<210> SEQ ID NO 3
<211> LENGTH: 18
<212> TYPE: PRT
<213> ORGANISM: Homo sapiens

<400> SEQUENCE: 3

Gln Gly His Phe Tyr Gly Glu Thr Ala Ala Val Tyr Val Ala Val Glu
1               5                   10                  15

Glu Arg

<210> SEQ ID NO 4
<211> LENGTH: 12
<212> TYPE: PRT
<213> ORGANISM: Homo sapiens

<400> SEQUENCE: 4

His Tyr Asp Gly Ser Tyr Ser Thr Phe Gly Glu Arg
1               5                   10

<210> SEQ ID NO 5
<211> LENGTH: 10
<212> TYPE: PRT
<213> ORGANISM: Homo sapiens

<400> SEQUENCE: 5

Gln Gly Ile Pro Phe Phe Gly Gln Val Arg
1               5                   10

<210> SEQ ID NO 6
<211> LENGTH: 10
<212> TYPE: PRT
<213> ORGANISM: Homo sapiens

<400> SEQUENCE: 6

Trp Leu Gln Gly Ser Gln Glu Leu Pro Arg
1               5                   10

<210> SEQ ID NO 7
<211> LENGTH: 7
<212> TYPE: PRT
<213> ORGANISM: Homo sapiens

```
<400> SEQUENCE: 7

Tyr Leu Thr Trp Ala Ser Arg
1               5

<210> SEQ ID NO 8
<211> LENGTH: 17
<212> TYPE: PRT
<213> ORGANISM: Homo sapiens

<400> SEQUENCE: 8

Gln Glu Pro Ser Gln Gly Thr Thr Thr Phe Ala Val Thr Ser Ile Leu
1               5                   10                  15

Arg
```